US009233926B2

(12) United States Patent
Mercola et al.

(10) Patent No.: US 9,233,926 B2
(45) Date of Patent: *Jan. 12, 2016

(54) COMPOUNDS FOR STEM CELL DIFFERENTIATION

(75) Inventors: Mark Mercola, La Jolla, CA (US); John Cashman, San Diego, CA (US); Marion Lanier, San Diego, CA (US); Erik Willems, San Diego, CA (US); Dennis Schade, Dorum (DE)

(73) Assignees: Sanford-Burnham Medical Research Institute, La Jolla, CA (US); Human Biomolecular Research Institute, San Diego, CA (US); ChemRegen, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/428,647

(22) Filed: Mar. 23, 2012

(65) Prior Publication Data
US 2013/0157947 A1 Jun. 20, 2013

Related U.S. Application Data

(63) Continuation-in-part of application No. 13/107,592, filed on May 13, 2011, now abandoned, which is a continuation-in-part of application No. 12/561,235, filed on Sep. 16, 2009, now Pat. No. 9,012,217.

(60) Provisional application No. 61/097,823, filed on Sep. 17, 2008.

(51) Int. Cl.
*C07D 215/38* (2006.01)
*A61K 31/47* (2006.01)
*C07D 215/54* (2006.01)

(52) U.S. Cl.
CPC .................................. *C07D 215/54* (2013.01)

(58) Field of Classification Search
CPC .................................................... C07D 215/54
See application file for complete search history.

(56) References Cited

U.S. PATENT DOCUMENTS

| 5,455,253 | A | 10/1995 | Ohnmacht, Jr. et al. | |
|---|---|---|---|---|
| 6,121,284 | A | * | 9/2000 | Urbahns et al. ............... 514/311 |
| 6,194,428 | B1 | 2/2001 | Urbahns et al. | |
| 8,716,319 | B2 | * | 5/2014 | Abelman et al. ............... 514/356 |
| 2005/0214939 | A1 | 9/2005 | Gold et al. | |
| 2007/0254359 | A1 | 11/2007 | Rezania et al. | |
| 2010/0159596 | A1 | 6/2010 | Mercola et al. | |

FOREIGN PATENT DOCUMENTS

| WO | WO 2008/056166 A2 | 5/2008 |
|---|---|---|
| WO | WO 2008/070875 A2 | 6/2008 |
| WO | WO 2008070875 A2 * | 6/2008 |
| WO | WO 2009/006580 A1 | 1/2009 |

OTHER PUBLICATIONS

Wang, L.-M. Tetrahedron 2005 vol. 61 pp. 1539-1543.*
CAPLUS 1981 497547.*
Berge, S. J. Pharm Sci 1977 vol. 66 pp. 1-19.*
Reddy and Raghu, "Facile $ZrCl_4$ promoted four-component coupling one-pot synthesis of polyhydroquinoline derivatives through unsymmetric Hantzsch reaction", *Indian Journal of Chemistry*, 47B(10): 1578-1582 (2008).
Su et al., "5-Pyrrolidin-2-yltetrazole-Promoted One-Pot Hantzsch Polyhydroquinoline Synthesis Using $NH_4HCO_3$ as Nitrogen Source", *Australian Journal of Chemistry*, 61(11):860-863 (2008).
Zhou et al., "Synthesis of Chiral Ethyl 5-(Acetoxyimino)-2,7,7-trimethyl-4-(1-naphthyl)-5,6,7,8-tetrahydroquinoline-3-carboxylate via Lipase-Catalyzed Hydrolysis", Synlett 2008(13):1999-2004 (2008).
Supplementary European Search Report from EP 09 81 5151, Dec. 7, 2012.
Takahashi et al., "Ascorbic acid enhances differentiation of embryonic stem cells into cardiac myocytes", *Circulation.*, 107(14):1912-6 (2003).
International Search Report (ISR) from PCT/US2012/037658, 2012.
Lemming et al., "The Role of Potassium Channels in Neuronal Differentiation of Stm Cells from Umbilical Cord Matrix", *The FASEB Journal*, Apr. 2008, vol. 22, Meeting Abstracts, 1197.11 (abstract only).

* cited by examiner

*Primary Examiner* — Heidi Reese
(74) *Attorney, Agent, or Firm* — DLA Piper LLP (US)

(57) ABSTRACT

Small molecule compounds and methods for stem cell differentiation are provided herein. An example of a class of compounds that may be used to practice the methods disclosed herein is represented by enantiomerically pure isomers of compounds of Formula I:

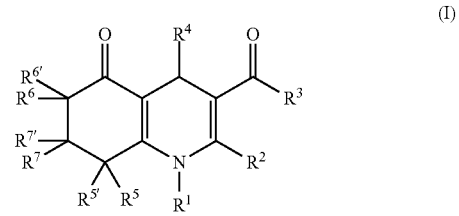

or a chirally pure stereoisomer, pharmaceutically acceptable salt, or solvate thereof, wherein $R^1$, $R^2$, $R^3$, $R^4$, $R^5$, $R^{5'}$, $R^6$, $R^{6'}$, $R^7$, $R^{7'}$ are as described herein.

12 Claims, 2 Drawing Sheets

COMPOUNDS FOR STEM CELL DIFFERENTIATION

CROSS REFERENCE TO RELATED APPLICATION(S)

This application is a continuation-in-part of U.S. patent application Ser. No. 13/107,592, filed on May 13, 2011 now abandoned, which is a continuation-in-part of U.S. patent application Ser. No. 12/561,235, filed on Sep. 16, 2009 now U.S. Pat. No. 9,012,217, which claims the benefit under 35 USC §119(e) to U.S. Provisional Patent Application Ser. No. 61/097,823, filed on Sep. 17, 2008, now abandoned. The disclosure of each of the prior applications is considered part of, and is incorporated by reference in, the disclosure of this application.

GRANT INFORMATION

This invention is made with government support under Comprehensive NIH Grant Nos. HL071913 and HL059502 awarded by the National Institutes of Health. The Government has certain rights in the invention.

FIELD OF THE DISCLOSURE

The disclosure relates generally to small molecule compounds and more specifically to enantiomerically pure derivatives of dihydropyridines and their use in stem cell differentiation.

BACKGROUND OF THE DISCLOSURE

Stem cells are a type cells that could be a source for the replacement of damaged or diseased tissues, and embryonic stem cells (ESCs) are a type of stem cells attracting particular interest. It has been previously shown that embryonic stem cells have the capacity to differentiate into many different cell types including heart, bone, neurons, liver tissue, and the like, both in vitro and in vivo. The differentiation potential of these cells has created substantial interest, since embryonic stem cells can thus provide a resource for replacing diseased cells for regenerating purposes.

ESCs are pluripotent cells which are derived from the inner cell mass of a blastocyst. The unique characteristics of ESCs are their capacities to regenerate themselves and to be capable of developing into various cell types of all three embryonic germ layers, ectoderm, mesoderm and endoderm, under appropriate environments. Such differentiated cell types include, but are not limited to, muscle, nerve, heart, liver, bone and blood. The potential of ESCs, induced pluripotent stem cells (iPSCs), adult or tissue specific stem cells and the like to grow into specialized cells attracts interest for research and disease treatment using these cells. The clinical application of stem cells involves harvest of the cells and transplantation of cells into failing organs to restore the function of the organs with or without prior in vitro differentiation.

Adult cardiomyocytes retain little, if any, ability to replicate, thus, heart failure is principally a disease of cardiomyocyte loss. No stem cell therapies to date have yielded significant replacement. Rather, transplanted cells, if they persist, produce endothelial cells or fibroblasts, and their reported ameliorating effects on heart function are probably the consequence of improvements in contractility, perfusion or other impaired processes. Replacement strategies by transplantation or stimulation of endogenous regeneration have been hypothesized. Whether endogenous cardiomyocyte stem cells exist and can be mobilized remains controversial, although a few populations have been proposed. Cardiomyocytes have potential in restoring heart function after myocardial infarction or in heart failure. Human embryonic stem cells (hESCs) are a potential source of transplantable cardiomyocytes but detailed comparison of hESC-derived cardiomyocytes with primary human cardiomyocytes is necessary before transplantation into patients becomes feasible.

While a clear alternative is to use hESCs, their cardiomyocyte yields are currently low. Generating sufficient new myocytes is a major obstacle when 25% of the ~4 billion cardiomyocytes in the average left ventricle are lost in infarction-induced heart failure. Transplanted cell survival is currently about 5%, thus improving replication of committed precursors either pre- or post-implantation is essential. Interestingly, transplanted hESC-derived cardiomyocytes tend to retain some proliferative capacity, perhaps due to their relative immaturity; however, the number of engrafted cells remains small in all studies to date, thereby reinforcing the need for molecules that promote cell division.

The American Diabetes Association estimates that there are currently 5 million people in the United States with confirmed diabetes, and over 10 million at risk. The cost of this disease and its sequelae to the American economy is staggering. Care of diabetics consumes a total of $98 billion per year, accounting for one of every seven healthcare dollars spent in the U.S. There are 24,000 new cases of diabetes-caused blindness caused by diabetes each year. Diabetes is the leading cause of kidney failure, contributing about 40% of new dialysis patients. Diabetes is also the most frequent cause of lower limb amputation, with 56,000 limbs lost to diabetes each year. The per capita health care costs incurred per diabetic person is $10,071 annually, compared with $2,669 for non-diabetics.

Type I diabetes mellitus (also known as insulin-dependent diabetes) is a severe condition accounting for 5-10% all diabetics. The pathology arises because the patient's insulin-secreting beta cells in the pancreas have been eliminated by an autoimmune reaction. Under current practice, the condition is managed by regular injection of insulin, constant attention to diet, and continuous monitoring of blood glucose levels to adjust the insulin dosing. It is estimated that the market for recombinant insulin will reach $4 billion by 2005. Of course, the availability of insulin is life-saving for Type I diabetics. But there is no question that the daily regimen of administration and monitoring that diabetics must adhere to is troublesome to the end user, and not universally effective.

Developmental work has been done in several institutions to capitalize on the promise of pluripotent stem cells from the embryo to differentiate into other cell types. Cells bearing features of the islet cell lineage have reportedly been derived from embryonic cells of the mouse. Thus, it is necessary to develop new paradigms to differentiate human pluripotent cells into fully functional differentiated cell types.

SUMMARY OF THE DISCLOSURE

In one aspect, the disclosure provides a compound of Formula I:

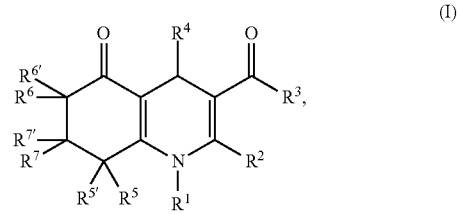

or a chirally pure stereoisomer, pharmaceutically acceptable salt or solvate thereof, wherein:

$R^1$ is independently hydrogen, $(C_1-C_6)$alkyl or a moiety forming a salt;

$R^2$ is independently hydrogen or $(C_1-C_6)$alkyl;

$R^3$ is independently $OR^8$ or $NR^{13}R^{13'}$;

$R^4$ is independently substituted or unsubstituted aryl, heteroaryl, heteroalkyl, heterocycloalkyl, or heteroaryl preferentially a phenyl, pyridine, wherein aryl, or heteroaryl is optionally independently substituted with 1 to 3 $R^9$ substituents;

$R^5$, $R^{5'}$, $R^6$, $R^{6'}$, $R^7$, and $R^{7'}$ are each independently hydrogen or $(C_1-C_6)$alkyl, aryl, heteroaryl;

$R^8$, $R^{13}$, and $R^{13'}$ are each independently hydrogen, $(C_1-C_6)$alkyl, $(C_3-C_8)$cycloalkyl, substituted or unsubstituted heterocyclyl, aryl, $(C_1-C_6)$alkylaryl, $CH_2CF$ alkyl$NR^{10}R^{10'}$;

each $R^9$ is independently hydrogen, halogen, $CF_3$, $(C_1-C_6)$alkyl, $(C_1-C_6)$alkoxy, cyclo$(C_1-C_6)$alkyl, substituted or unsubstituted aryl or heteroaryl, more specifically a substituted or unsubstituted phenyl, substituted or unsubstituted pyridine, substituted or unsubstituted indolyl; substituted or unsubstituted pyrrolidinyl, or substituted or unsubstituted piperidinyl, wherein phenyl, pyridine, indolyl, pyrrolidinyl and piperidinyl are each optionally independently substituted with hydrogen, halogen, $CF_3(C_1-C_6)$alkoxy, or $(C_1-C_6)$alkyl; and $R^{10}$ and $R^{10'}$ are each independently hydrogen, $(C_1-C_6)$alkyl, aryl, or $(C_1-C_6)$alkylaryl.

In another aspect the disclosure provides methods for producing differentiated cells from stem cells by contacting the stem cells with a compound of Formula I.

In another aspect the disclosure provides methods for stem cell differentiation, comprising contacting the embryonic stem cells with a dihydropyridine-based enantiomeric compound of structure IA in the form of a free base or a pharmaceutically acceptable salt, hydrate, solvate or N-oxide thereof, wherein $R^1$, $R^2$, $R^{2'}$, $R^3$, $R^4$, $R^5$, $R^{5'}$, $R^6$, $R^{6'}$, $R^7$, and $R^{7'}$ are as described above.

In another aspect the disclosure provides methods for stem cell differentiation and class driving cardiogenesis in ESC (mouse and human) by inhibition of TGF-beta signaling, comprising contacting the embryonic stem cells with a dihydropyridine-based enantiomeric compound of structure IA in the form of a free base or a pharmaceutically acceptable salt, hydrate, solvate or N-oxide thereof, racemic or enantiomerically pure, wherein $R^1$, $R^2$, $R^{2'}$, $R^3$, $R^4$, $R^5$, $R^{5'}$, $R^6$, $R^{6'}$, $R^7$, and $R^{7'}$ are as described above.

In another aspect the disclosure provides methods for the selective inhibition of TGF-beta, without affecting the closely related Activin A pathway, by degrading Type II TGFB receptors, comprising contacting the embryonic stem cells with a dihydropyridine-based enantiomeric compound of structure IA in the form of a free base or a pharmaceutically acceptable salt, hydrate, solvate or N-oxide thereof, racemic or enantiomerically pure, wherein $R^1$, $R^2$, $R^{2'}$, $R^3$, $R^4$, $R^5$, $R^{5'}$, $R^6$, $R^{6'}$, $R^7$, and $R^{7'}$ are as described above.

In another aspect, the disclosure provides methods for inhibition of TGF-beta, comprising contacting the embryonic stem cells either ex vivo or in vivo with a dihydropyridine-based enantiomeric compound of structure IA in the form of a free base or a pharmaceutically acceptable salt, hydrate, solvate or N-oxide thereof, racemic or enantiomerically pure, wherein $R^1$, $R^2$, $R^{2'}$, $R^3$, $R^4$, $R^5$, $R^{5'}$, $R^6$, $R^{6'}$, $R^7$, and $R^{7'}$ are as described above.

In another aspect the disclosure provides methods for TGFb inhibition that may be of importance to treat numerous diseases for which decreasing TGFb might be beneficial, including lung cancer, tissue fibrosis, myocardial infarction and other diseases, comprising contacting the embryonic stem cells with a dihydropyridine-based enantiomeric compound of structure IA in the form of a free base or a pharmaceutically acceptable salt, hydrate, solvate or N-oxide thereof, racemic or enantiomerically pure wherein $R^1$, $R^2$, $R^{2'}$, $R^3$, $R^4$, $R^5$, $R^{5'}$, $R^6$, $R^{6'}$, $R^7$, and $R^{7'}$ are as described above. In these instances these compounds or analogues could be used as a drug.

In another aspect the disclosure provides methods for induction of TGFb receptor degradation TGFb inhibition that may be of importance to treat numerous diseases for which decreasing TGFb might be beneficial, including lung or other cancers, tissue fibrosis, myocardial infarction and other diseases, comprising contacting the embryonic stem cells with a dihydropyridine-based compound of structure IA in the form of a free base or a pharmaceutically acceptable salt, hydrate, solvate or N-oxide thereof, racemic or enantiomerically pure wherein $R^1$, $R^2$, $R^{2'}$, $R^3$, $R^4$, $R^5$, $R^{5'}$, $R^6$, $R^{6'}$, $R^7$, $R^{7'}$ are as described above particularly 'Inducer of TGFβ Receptor 2 degradation' (ITD)

DETAILED DESCRIPTION OF THE DISCLOSURE

Figure 1:
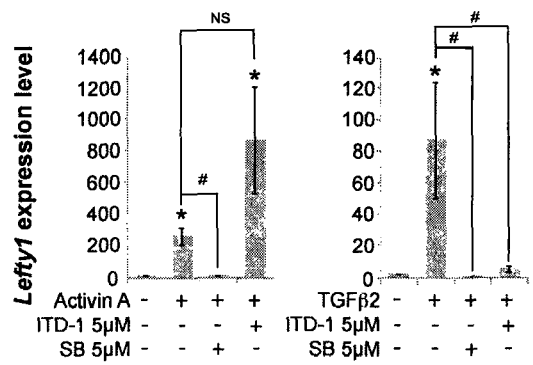
FIG. 1 is a graphic representation of TGFb Selectivity of ITD, illustrated by Lefty1 induction.

The following terms, definitions and abbreviations apply. Abbreviations used herein have their conventional meaning within the chemical and biological arts.

The term "lipophilic" refers to moieties having an affinity for lipids and other fat-like substances, tending to combine with, and capable of dissolving, them.

The term "cardiomyocytes" refers to cells of muscular tissue in the heart.

The term "embryonic stem cell" refers to cell from the inner group of cells of an early embryo (blastocyst), with the potential to become most or all of the body tissues.

The term "stem cell differentiation" refers to series of events involved in the development of specialized cells from stem cells, where the specialized cells have specific structural, functional, and biochemical properties.

The term "patient" refers to organisms to be treated by the methods of the disclosure. Such organisms include, but are not limited to, humans. In the context of the disclosure, the term "subject" generally refers to an individual who will receive or who has received treatment described below (e.g., administration of the compounds of the disclosure, and optionally one or more additional therapeutic agents).

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched chain, or cyclic hydrocarbon radical, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by —$CH_2CH_2CH_2CH_2$—, $CH_2CH$=$CHCH_2$—, —$CH_2CCCH_2$—, —$CH_2CH_2CH(CH_2CH_2CH_3)CH_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR, and/or —$SO_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings, which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g., "3 to 7 membered"), the term "member" refers to a carbon or heteroatom.

The term "oxo" as used herein means an oxygen that is double bonded to a carbon atom.

The terms "heterocycle" and "heterocyclic" refer to a monovalent unsaturated group having a single ring or multiple condensed rings, from 1 to 8 carbon atoms and from 1 to 4 heteroatoms, for example, nitrogen, sulfur or oxygen within the ring.

The term "methylthio" refers to a moiety —S—CH$_3$.

The term "dihydropyridine" refers to compound A shown below, as well as to the moieties derived from compound A:

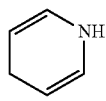

A

The terms "furyl," "tetrahydrofuryl," and "pyridyl" refer to radicals formed by removing one hydrogen from the molecules of furan, tetrahydrofuran, and pyridine, respectively.

The terms "alkyl amine" and "cyclic amine" refer to alkanes or cycloalkanes, respectively, having one hydrogen substituted by a primary, secondary or tertiary amino group, as well as to the moieties and radicals derived from such amines.

The term "alkyl amide" refers to alkanes, having one hydrogen substituted by a primary, secondary or tertiary amino group.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', ═O, ═NR', ═N—OR', —NR'R", —SR', -halogen, —SiR'R"R''', —OC(O)R', —C(O)R', —CO2R', —C(O)NR'R", —OC(O)NR'R", —NR"C(O)R', —NR'—C(O)NR"R''', —NR"C(O)OR', —NR—C(NR'R")═NR''', —S(O)R', —S(O)$_2$R', —S(O)2NR'R", —NRSO$_2$R', —CN and —NO$_2$ in a number ranging from zero to (2m'+1), where m' is the total number of carbon atoms in such radical. R', R", R''' and R'''' each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the disclosure includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

The term "alkoxy" refers to the moiety —O— alkyl, wherein alkyl is as defined above. Examples of alkoxy structures that are within the purview of the definition include, but are not limited to, (C$_1$-C$_6$)alkoxy radicals, such as methoxy, ethoxy, propoxy, isopropoxy, butoxy, iso-butoxy, sec-butoxy, tert-butoxy, pentoxy, 3-pentoxy, or hexyloxy.

Similar to the substituents described for alkyl radicals above, exemplary substituents for aryl and heteroaryl groups (as well as their divalent derivatives) are varied and are selected from, for example: halogen, —OR', —NR'R", —SW, -halogen, —SiR'R"R''', —OC(O)R', —C(O)R', —CO2R', —C(O)NR'R", —OC(O)NR'R", —NR"C(O)R', —NR'—C(O)NR"R''', —NR"C(O)OR', —NR—C(NR'R"R''')═NR'''', —NR—C(NR'R")═NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R", R''' and R'''' are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R''' and R'''' groups when more than one of these groups is present.

Two of the substituents on adjacent atoms of aryl or heteroaryl ring may optionally form a ring of the formula -T-C(O)—(CRR')q-U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)r-B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from the following moieties: (A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from: (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The compounds of the disclosure may exist as salts. Examples of applicable salt forms include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When the disclosed compounds contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the disclosure contain both basic and acidic functionalities that allow the compounds to be converted into either base or acid addition salts.

The term "pharmaceutically acceptable salt" refers to salts that may be used where the compounds used in the methods of the disclosure are sufficiently basic or acidic to form stable nontoxic acid or base salts. Examples of pharmaceutically acceptable salts include organic acid addition salts formed with acids which form a physiological acceptable anion, for example, oxalate, tosylate, methanesulfonate, acetate, citrate, malonate, tartarate, succinate, benzoate, ascorbate, ketoglutarate, and glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example by treating a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the disclosure can exist in unsolvated forms as well as solvated forms, including hydrated forms. In general, the solvated forms are equivalent to unsolvated forms and are encompassed within the scope of the disclosure. Certain compounds of the disclosure may exist in multiple crystalline or amorphous forms. In general, all physical forms are equivalent for the uses contemplated by and are intended to be within the scope of the disclosure.

Certain compounds of the disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the disclosure. The compounds of the disclosure do not include those which are known in art to be too unstable to synthesize and/or isolate. The disclosure is meant to include compounds in racemic and optically pure forms in particular attached to the $R^4$ substituent of compound of Formula I. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another. It will be apparent to one skilled in the art that certain compounds of the disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the disclosure.

The compounds of the disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C).

All isotopic variations of the compounds of the disclosure, whether radioactive or not, are encompassed within the scope of the disclosure.

The term "pharmaceutically acceptable salts" is meant to include salts of active compounds which are prepared with relatively nontoxic acids or bases, depending on the particular substituent moieties found on the compounds described herein. When compounds of the disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the disclosure contain both basic and acidic functionalities that allow the compounds to be converted into either base or acid addition salts.

In addition to salt forms, the disclosure provides compounds, which are in a prodrug form. Prodrugs of the compounds described herein are those compounds that readily undergo chemical changes under physiological conditions to provide the compounds of the disclosure. Additionally, prodrugs can be converted to the compounds of the disclosure by chemical or biochemical methods in an ex vivo environment. For example, prodrugs can be slowly converted to the compounds of the disclosure when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" in reference to a particular disease includes prevention of the disease.

The disclosure also provides articles of manufacture comprising packaging material and a pharmaceutical composition contained within said packaging material, wherein said packaging material comprises a label which indicates that said pharmaceutical composition can be used for treatment of disorders and wherein said pharmaceutical composition comprises a compound according to the disclosure.

The disclosure also provides pharmaceutical compositions comprising at least one compound in an amount effective for treating a disorder, and a pharmaceutically acceptable vehicle or diluent. The compositions of the disclosure may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the disclosure may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the disclosure include amine salts formed by the protonation of an amino group with inorganic acids such as hydrochloric acid, hydrobromic acid, hydroiodic acid, sulfuric acid, phosphoric acid, and the like. Salts of the disclosure may also include amine salts formed by the protonation of an amino group with suitable organic acids, such as p-toluenesulfonic acid, acetic acid, and the like. Additional excipients which are contemplated for use in the practice of the disclosure are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs, hydrates, and solvates of the compounds are included in the disclosure.

The disclosed pharmaceutical compositions may be administered by any suitable means, for example, orally, such as in the form of tablets, capsules, granules or powders; sublingually; buccally; parenterally, such as by subcutaneous, intravenous, intramuscular, intrathecal, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

In addition to primates, such as humans, a variety of other mammals can be treated according to the method of the disclosure. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The term "therapeutically effective amount" means the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the disclosure or pharmaceutical composition to the subject in need of treatment.

"TGFb" means Transforming Growth Factor beta, a growth factor.

"TGFb selective" means the compound blocks the TGFb pathway to a greater extent than the related signal Actvin A/Nodal "TGFBR2 degradation" means that the TGFb type II receptor is degraded to the proteasome specifically.

"ITD" is a novel name for some DHP subsets based on their functional activity, (i.e., Inducer of TGFBR2 degradation).

The pharmaceutical compositions for the administration of the compounds of this embodiment either alone or in combination with other agents, e.g., chemotherapeutic, may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Also useful as a solubilizer is polyethylene glycol, for example. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent or cosolvent or complexing agent or dispersing agent or excipient or combination thereof, for example 1,3-butane diol, polyethylene glycols, polypropylene glycols, ethanol or other alcohols, povidones, Tweens, sodium dodecyle sulfate, sodium deoxycholate, dimethylacetamide, polysorbates, poloxamers, cyclodextrins, e.g., sulfobutyl ether β-cyclodextrin, lipids, and excipients such as inorganic salts (e.g., sodium chloride), buffering agents (e.g., sodium citrate, sodium phosphate), and sugars (e.g., saccharose and dextrose). Among the acceptable vehicles and solvents that may be employed are water, dextrose solutions, Ringer's solutions and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration. For injection, the pharmaceutical compositions of the disclosure may be formulated in aqueous solutions, for example, in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

The compounds of the disclosure may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. For topical use, creams, ointments, jellies, solutions or suspensions, etc., containing the compounds of the disclosure are employed. For purposes of this application, topical application shall include mouthwashes and gargles.

In the methods described herein, an appropriate dosage level will generally be about 0.01 to 500 mg per kg patient body weight per day which can be administered in single or multiple doses. The dosage level can be about 0.01 to about 250 mg/kg per day, such as 0.01 to about 100 mg/kg per day, for example, 0.01 to about 10 mg/kg per day, such as 0.04 to about 5 mg/kg per day, or about 0.5 to about 100 mg/kg per day. A suitable dosage level may be also about 0.05 to 100 mg/kg per day, or 0.1 to 50 mg/kg per day or 1.0 mg/kg per day. Within this range the dosage may be 0.05 to 0.5, 0.5 to 5 or 5 to 50 mg/kg per day for example. The Examples section shows that one of the exemplary compounds was dosed at 0.1 mg/kg/day while another was effective at about 1.0 mg/kg/day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or once or twice per day. There may be a period of no administration followed by another regimen of administration. Administration of the compounds may be closely associated with the schedule of a second agent of administration.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one embodiment the disclosure provides a compound of Formula I:

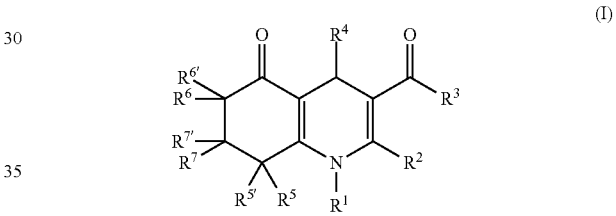

(I)

or a chirally pure stereoisomer, pharmaceutically acceptable salt, or solvate thereof,
wherein:
$R^1$ is independently hydrogen, $(C_1-C_6)$alkyl or a moiety forming a salt;
$R^2$ is independently hydrogen, $(C_1-C_6)$alkyl;
$R^3$ is independently $OR^8$ or $NR^{13}R^{13'}$;
$R^4$ is independently substituted or unsubstituted aryl, heteroalkyl, heterocycloalkyl, or heteroaryl, indolyl, phenyl, substituted or unsubstituted pyridine, wherein phenyl or pyridine is optionally independently substituted with 1 to 3 $R^9$ substituents;
$R^5$, $R^{5'}$, $R^6$, $R^{6'}$, $R^7$, and $R^{7'}$ are each independently hydrogen or $(C_1-C_6)$alkyl;
$R^8$, $R^{13}$, and $R^{13'}$ are each independently hydrogen, $(C_1-C_6)$alkyl, $(C_3-C_8)$cycloalkyl, substituted or unsubstituted heterocyclyl, aryl, $(C_1-C_6)$alkylaryl, or $(C_1-C_6)$alkylNR$^{10}$R$^{10'}$;
each $R^9$ is independently hydrogen, halogen, $(C_1-C_6)$alkyl, $(C_1-C_6)$alkoxy, cyclo$(C_1-C_6)$alkyl, substituted or unsubstituted phenyl, substituted or unsubstituted pyridine, substituted or unsubstituted indolyl; substituted or unsubstituted pyrrolidinyl, or substituted or unsubstituted piperidinyl, wherein phenyl, pyridine, indolyl, pyrrolidinyl and piperidinyl are each optionally independently substituted with hydrogen, halogen, or $(C_1-C_6)$alkyl; and
$R^{10}$ and $R^{10'}$ are each independently $(C_1-C_6)$alkyl, aryl, or $(C_1-C_6)$alkylaryl.

In another aspect the disclosure provides a compound of Formula I, wherein $R^1$ is hydrogen; $R^2$ is hydrogen, CH$_3$ or CH$_2$CH$_3$; R$^3$ is OR$^8$; R$^4$ is substituted or unsubstituted phenyl; R$^8$ is hydrogen, C$_1$-C$_6$-alkyl optionally substituted by

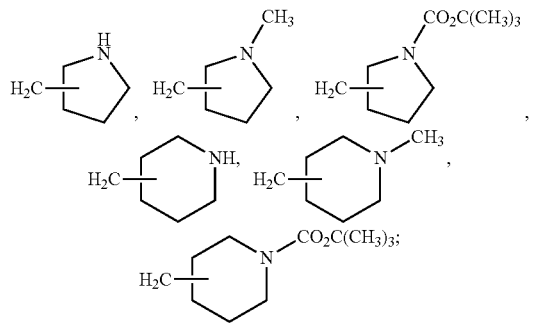

and each R$^9$ is independently hydrogen, F, Cl, Br, or I.

In another aspect the disclosure provides a compound of Formula I, wherein R$^8$ is CH$_3$, CH$_2$CH$_3$,

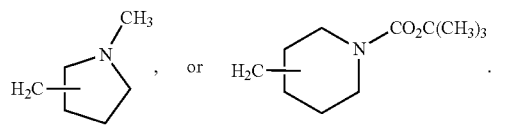

In another aspect the disclosure provides a compound of Formula IB:

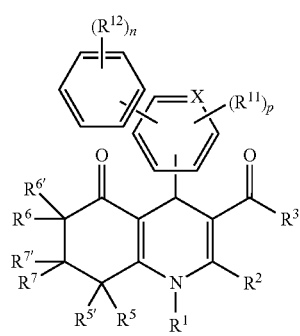

or a pharmaceutically acceptable salt or solvate thereof, wherein X is CH or N; p is an integer from 0 to 4; n is an integer from 0 to 5; and each R$^{11}$ and R$^{12}$ are each independently hydrogen, halogen, or (C$_1$-C$_6$)alkyl.

In another aspect the disclosure provides a compound of Formula IB, wherein X is CH; R$^1$ is hydrogen; R$^2$ is hydrogen, CH$_3$ or CH$_2$CH$_3$; R$^3$ is OR$^8$; R$^8$ is CH$_3$, CH$_2$CH$_3$,

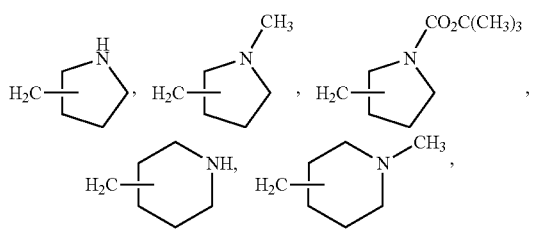

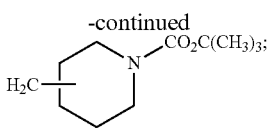

and R$^{11}$ and R$^{12}$ are each independently hydrogen, F, Cl, Br, I, CH$_3$ or CH$_2$CH$_3$.

In another aspect the disclosure provides a compound of Formula I, wherein R$^8$ is CH$_3$, CH$_2$CH$_3$,

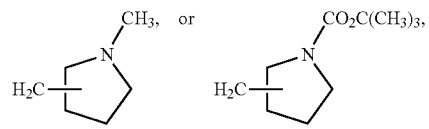

In another aspect the disclosure provides a compound of Formula IC:

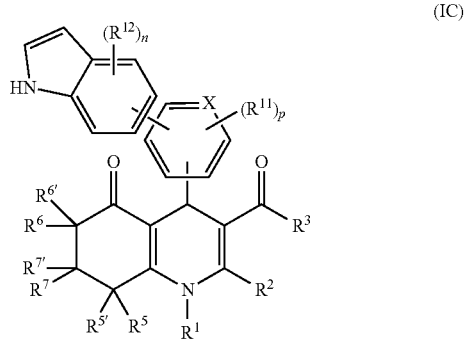

or a pharmaceutically acceptable salt thereof, wherein X is CH or N; p is an integer from 0 to 4; n is an integer from 0 to 3; and each R$^{11}$ and R$^{12}$ are each independently hydrogen, halogen, or (C$_1$-C$_6$)alkyl.

In another aspect the disclosure provides a compound of Formula IC and both enantiomers about the R$^4$ carbon atom, wherein R$^1$ is hydrogen; R$^2$ is hydrogen, CH$_3$ or CH$_2$CH$_3$; R$^3$ is OR$^B$; R$^8$ is CH$_3$, CH$_2$CH$_3$,

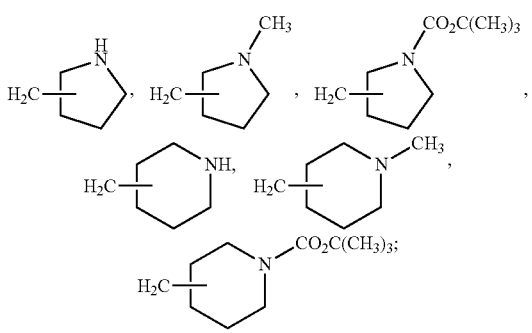

and R$^{11}$ and R$^{12}$ are each independently hydrogen, F, Cl, Br, I, CH$_3$ or CH$_2$CH$_3$.

Some specific dihydropyridine-based compounds within structure I include, but are not limited to, compounds I-22 that are pure enantiomers at the carbon atom attached to R$^4$

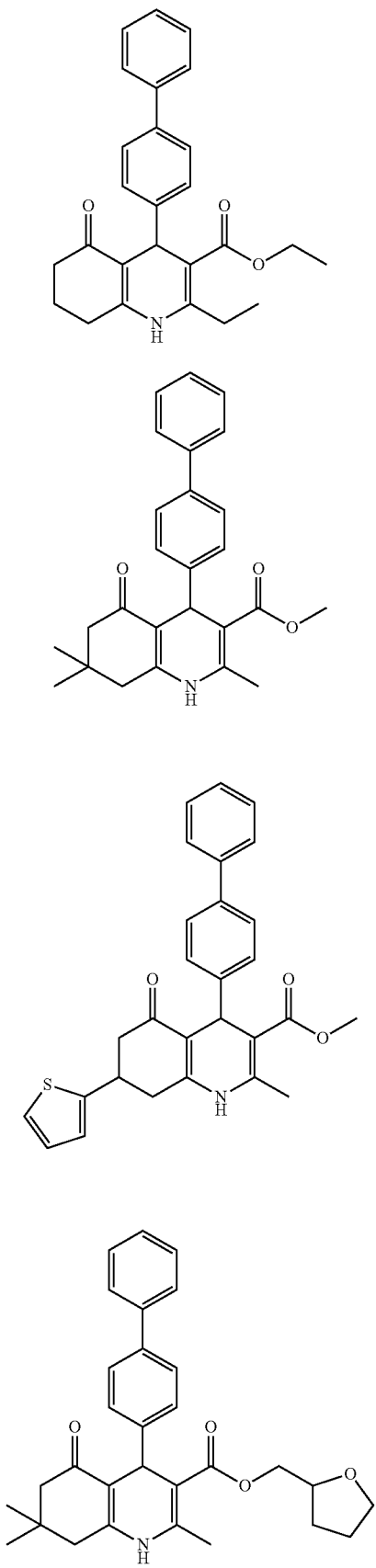
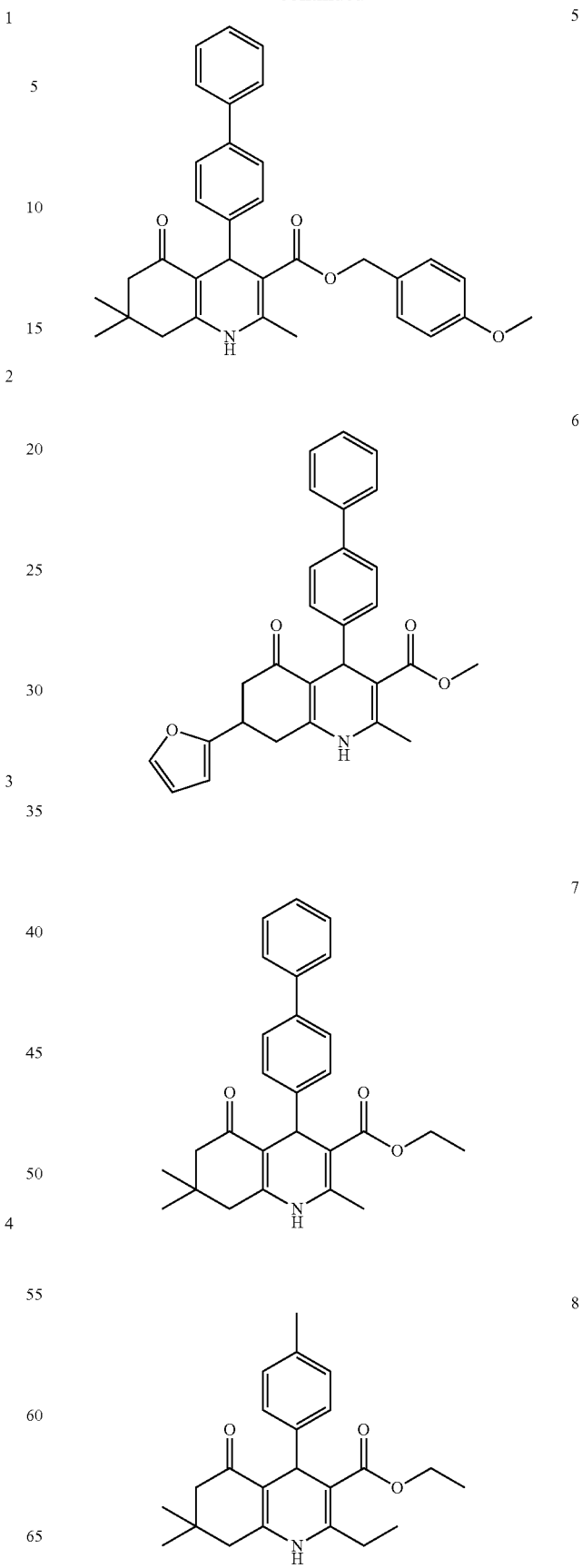

-continued
9
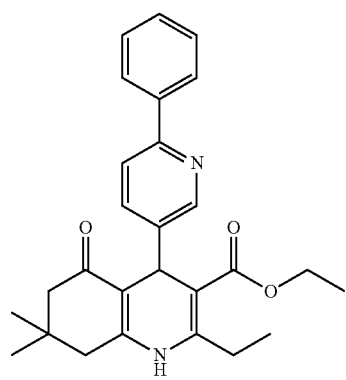
10
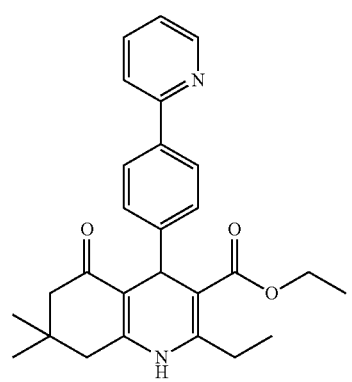
11
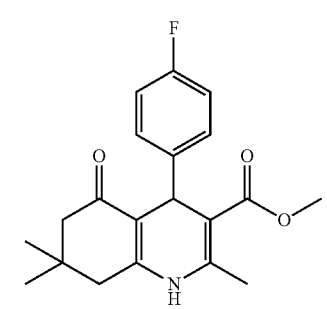
12
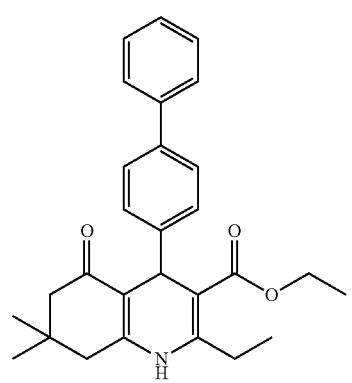
-continued
13
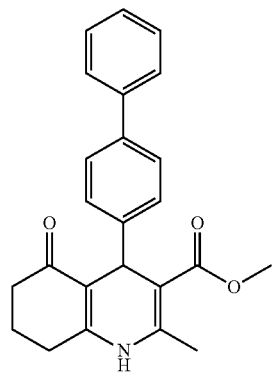
14
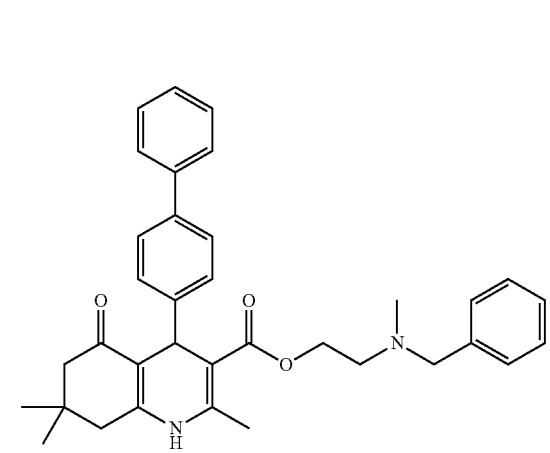
15
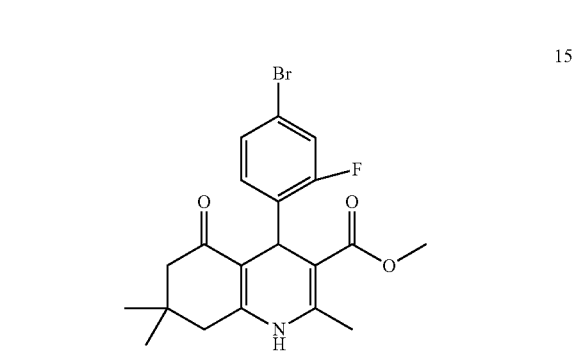
16
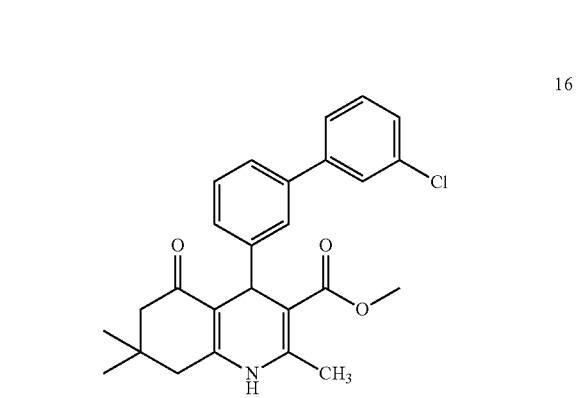

17

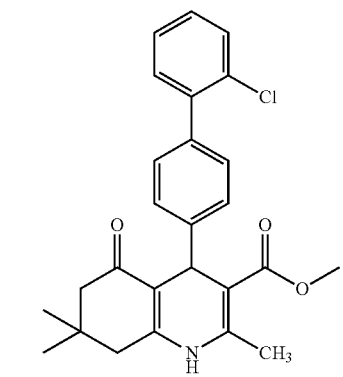

18

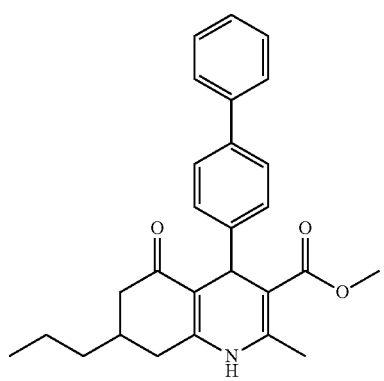

19

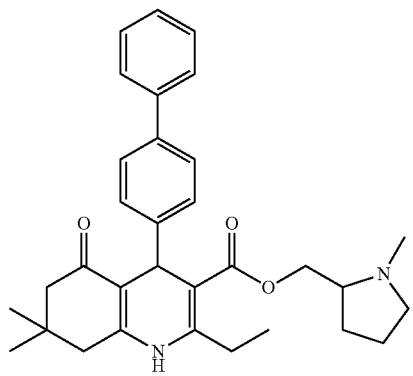

20

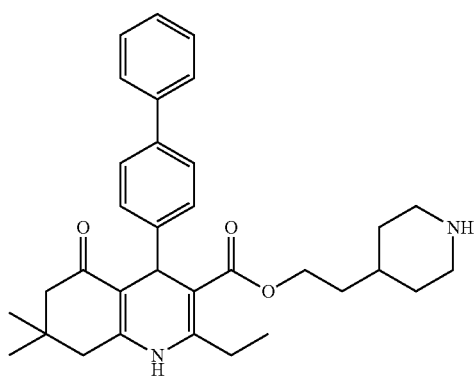

21

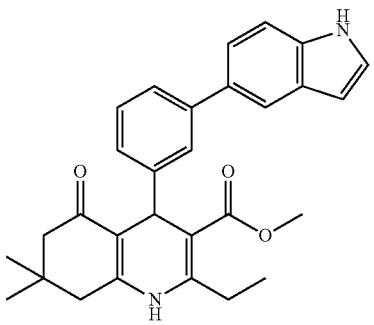

22

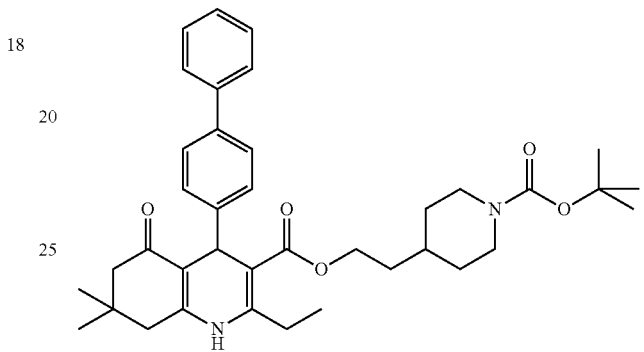

In another aspect the disclosure provides compounds of Formula I, wherein the pharmaceutically acceptable salt is the salt of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (-L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (-L), salicylic acid, sebacic acid, stearic acid, succinic acid, sulfuric acid, tartaric acid (+L), thiocyanic acid, toluenesulfonic acid (p), or undecylenic acid.

In another aspect the disclosure provides methods for producing differentiated cells from stem cells by contacting the stem cells either ex vivo or in vivo with a compound of Formula I. By way of example, the differentiated cells may include, but are not limited to cardiomyocytes, hepatocytes or islet or neuronal cells.

In another aspect the disclosure provides methods for producing differentiated cells from stem cells by contacting the stem cells with a compound of Formula I, wherein contacting the stem cells with a compound of Formula I is from about 24 hours to about 192 hours or from about 48 to about 144 hours.

In yet another aspect, the differentiated cells are produced from stem cells by contacting the stem cells with a compound of Formula I, and further contacting the cells with Activin A.

In another aspect the disclosure provides methods for producing differentiated cells from stem cells by contacting the stem cells with a compound of Formula I, wherein the cells differentiate to mesoderm.

In another aspect the disclosure provides methods for producing differentiated cells from stem cells by contacting the stem cells with a compound of Formula I, further comprising contacting the cells with a Wnt protein including, but not limited to, Wnt3a, Wnt5a or Wnt7.

In another aspect the disclosure provides methods for producing differentiated cells from stem cells by contacting the stem cells with a compound of Formula I, wherein the stem cells are embryonic stem cells, induced pluripotent stem cells or adult stem cells.

In another aspect the disclosure provides for producing differentiated cells from stem cells by contacting the stem cells with a compound of Formula I, further comprising contacting the cells with a Bone Morphogenetic Protein.

In one aspect, the stem cells are produced by inhibition of TGFb, comprising contacting TGFb with a compound of structural Formula (I). In another aspect the disclosure provides methods for producing differentiated cells from stem cells by contacting the stem cells with of compound of Formula I, further comprising contacting the stem cells with a TGF-B protein. In some aspects the TGF-B protein is TGF-B1 or TGF-B2.

Also provided herein is a method for the treatment of a disease or disorder associated with TGF. The method includes administering to a subject in need thereof an effective amount of a compound of structural Formula (I). In certain aspects, the disease or disorder includes cancer, fibrosis, or vascular disease.

A method of selectively inhibiting TGFb is provided herein. The method includes contacting TGFBR2 with a compound of structural Formula (I). Compounds of structural Formula (I) may clear TGFBR2 from the cell's surface, thereby selectively inhibiting TGFb.

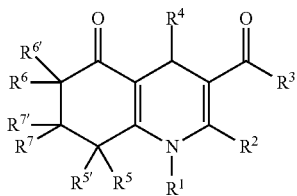

In another aspect the disclosure provides methods for producing differentiated cells from stem cells. The methods comprise contacting stem cells with the disclosed compounds that stimulate the production of differentiated cells thereby. The disclosed compounds may be used to carry out such methods include all the compounds within the above-described genera and sub-general I, including particular enantiomeric versions of species I, also described above.

In another aspect the disclosure provides methods for stem cell differentiation, comprising contacting the embryonic stem cells with a compound of structure I, in the form of free base or a pharmaceutically acceptable salt, hydrate, solvate or N-oxide thereof.

Those skilled in the art may determine the optimal time of contacting the stem cells and with the disclosed compounds described below required achieving the optimal results. As a guideline, the period of contact may be between about 24 hours and about 192 hours, for example, between about 48 hours and about 144 hours. Differentiated cells produced by the disclosed methods may include are cardiomyocytes, liver cells, lung cells, pancreatic cells, and others.

The stem cells suitable for use in the disclosed methods may be derived from a patient's own tissue. This would enhance compatibility of differentiated tissue grafts derived from the stem cells with the patient. In this context it should be noted that embryonic stem cells can include adult stem cells derived from a person's own tissue iPSCs, embryonic stem cells, and the like. Human stem cells may be genetically modified prior to use through introduction of genes that may control their state of differentiation prior to, during or after their exposure to the embryonic cell or extracellular medium from an embryonic cell. They may be genetically modified through introduction of vectors expressing a selectable marker under the control of a stem cell specific promoter, such as Oct-4. The stem cells may be genetically modified at any stage with a marker so that the marker is carried through to any stage of cultivation. The marker may be used to purify the differentiated or undifferentiated stem cell populations at any stage of cultivation.

The disclosure also provides differentiated cells produced according to the disclosed methods that may be used for transplantation, cell therapy or gene therapy. The disclosure further provides a differentiated cell produced according to the disclosed methods that may be used for therapeutic purposes, such as in methods of restoring cardiac function in a subject suffering from a heart disease or condition.

In another aspect the disclosure provides methods of treating or preventing a cardiac disease or condition, the method including introducing an isolated differentiated cardiomyocyte cell of the disclosure and/or a cell capable of differentiating into a cardiomyocyte cell when treated in accordance with the disclosed methods into cardiac tissue of a subject. The isolated cardiomyocyte cell may be transplanted into damaged cardiac tissue of a subject. The method may result in the restoration of cardiac function in a subject.

In another aspect the disclosure provides methods of repairing cardiac tissue, the method including introducing an isolated cardiomyocyte cell of the disclosure and/or a cell capable of differentiating into a cardiomyocyte cell when treated in accordance with the method of the disclosure into damaged cardiac tissue of a subject.

The subject may be suffering from a cardiac disease or condition. In the method of the disclosure, the isolated cardiomyocyte cell may be transplanted into damaged cardiac tissue of a subject. The method may result in the restoration of cardiac function in a subject. The disclosure also provides a myocardial model for testing the ability of stem cells that have differentiated into cardiomyocytes to restore cardiac function. The disclosure further provides a cell composition including a differentiated cell of the disclosure, and a carrier. The term "inducing differentiation" as used herein is taken to mean causing a stem cell to develop into a specific differentiated cell type as a result of a direct or intentional influence on the stem cell. Influencing factors in addition to the compounds described herein can include cellular parameters such as ion influx, a pH change and/or extracellular factors, such as secreted proteins, such as but not limited to growth factors and cytokines that regulate and trigger differentiation. It may include culturing the cell to confluence and may be influenced by cell density.

The stem cell and the cell providing the differentiating factor(s) may be co-cultured in vitro. This typically involves introducing the stem cell to an embryonic cell monolayer produced by proliferation of the embryonic cell in culture.

The cellular and molecular events regulating the induction and tissue-specific differentiation of endoderm are important to understanding the development and function of many organ systems. Stem cell-derived endoderm is important for the development of cellular therapies for the treatment of disease such as diabetes, liver cirrhosis, or pulmonary emphysema (e.g., via development of islet cells, hepatocytes or lung cells, respectively). Accordingly, compounds described in the disclosure find particular use in inducing differentiation of cells in the endoderm lineage, including pancreas, liver, lung and the like.

In one aspect, the compounds of the disclosure are used to screen for targets of their action. For example, competitive analyses can be performed using compounds with known targets. Such targets include, for example, but not limited to MEF2C; Beta-catenin; TCF/LEF; Smad2, Smad3; Smad4 (binding partners of the above proteins are also potential targets since they would modulate activity); p38, and components of the signaling that activate MEF2C; components of the Wnt pathway, such as Frizzled proteins, CaMK, Axin, Dishevelled, APC, GSK3, FRAP; Calmodulin (in particular for phenothiazine analogues); Potassium channel targets (in particular for dihydropyridine analogues); and Calcium channel targets (in particular for dihydropyridine analogues).

The invention describes the use of dihydropyridine molecules of Formula I to drive cardiogenesis in stem cells and that dihydropyridine molecules of Formula I do this by selectively inhibiting TGFb signaling.

Dihydropyridine molecules of Formula I inhibit the TGFb pathway selectively and do not functionally block related pathways such as Activin A/Nodal pathways.

The described TGFb inhibitors enantiomers of dihydropyridine molecules of Formula I serve as probes to study the TGFb pathway specifically in biological models, not limited to cancer, stem cell differentiation, animal models and fibrosis.

The use of dihydropyridine molecules of Formula I as TGFb inhibitors as drugs to treat disease that possess elevated TGFb levels underlying a disease. Not limited to lung cancer, fibrosis.

The use of the term inducer of TGFb receptor type II degradation (ITD) for compounds 7 (racemic, and single enantiomers), 46, and 37.

The disclosure also provides the means to treat any cell or tissue to inhibit TGFb in a method that would be clinically beneficial fibrosis, cancer, and other related diseases.

EXAMPLES

The embodiments of the disclosure may be further illustrated by the following non-limiting examples.

Example 1

Biological Assay for Cardiac Induction

The primary screen is conducted with CGR8 mESCs stably transfected with eGFP under control of the alpha myosin heavy chain (aMHC) promoter. The bioassay is run essentially as described (Bushway et al., Methods Enzymol, 414: 300, 2006). Briefly, cells were seeded onto Greiner 384 well microclear bottom microtiter plates in well volume at a density of ~229 cells/mm2. Compounds are administered on day 2 with ½ well volume at 2× concentration and mixed thoroughly with replacement on day 4 by aspiration and replacement of 1× concentrated compound in ½ well volume; otherwise, fresh media is replaced at ½ well volume every second day until the assay is complete. The primary assay is executed on the Beckman FX with robotic arm and integrated cytomats using SAMI scheduler.

The optimal time to stop the differentiation is empirically determined to be at day 9 of differentiation, when cardiomyocytes appear in positive control cultures that have higher density cells or culture the cells in embryoid body (not monolayer) culture. Plates were fixed for 5 minutes in 4% paraformaldehyde in 1×PBS, rinsed 3 times in 1×PBS (includes a DAPI stain). 50% glycerol is then added to each well and plates stored until imaging. A total of 30,000 data points were obtained. That is ~44,000 unique compounds were screened at 1 µg/mL and 5 m/mL, corresponding to approximately 2 µM and 13 µM (assuming approximate MW 300-500 g/mole). The primary screen imaging was done with Q3DM Eidaq 100 mounted with a 4× objective capturing 4 images/well at 8×8 binning. Plates were loaded manually. Image quantification is done using a simple image subtraction routine that subtracted the red channel images from the green (eGFP) channel images to remove background signal from the eGFP images. This algorithm yielded an integrated value for each well.

Follow-up confirmations and testing of hits for SAR were performed on the Hamilton STAR fluid handler with integrated Kendro Cytomat plate hotel and Kendro Cytomat plate incubators using the Hamilton STAR liquid handler robot. By the time of these later experiments, our imaging infrastructure and algorithms had changed. Imaging is done on the INCell 1000 (GE/Amersham) using a 10× objective capturing 9 images/well at 4×4 binning during image capture. Microtiter plate loading is automated using the CRS/Thermo Catalyst Express robotic arm and Polara scheduler. Image quantification is performed on captured TIFF images using the Developer Toolbox (GE/Amersham) with custom algorithms.

A biological time course experiment showed the biological action of each molecule was maximized at overlapping but non-identical developmental time periods between days 2 to 5 of mESC to cardiomyocyte differentiation. Early analysis of molecular markers induced in secondary assays showed that dihydropyridine molecules of Formula I act by regulating mesoderm and endodermal patterning, consistent with the time frame when they are active. An SAR effort to investigate the structure-activity relationship (SAR) of dihydropyridine molecules of Formula I provided an optimized structure yielding considerable biological potency. The medicinal chemistry and SAR studies for dihydropyridine molecules of Formula I are described.

The molecules would be expected to be used for stimulating differentiation of stem cell cells, in particular but not limited to embryonic stem cells (ESCs) and induced pluripotent stem cells (IPSCs) to endoderm (e.g., liver, lung and pancreas) and neuronal cells and cardiac derivatives.

In brief, each screen with dihydropyridine molecules of Formula I for stem cell differentiation used an image that was dynamically thresholded by acquiring a global pixel average and multiplying this value by a scalar to produce an image mask approximating the specific signal. The mask is used to collect integrated intensities in blue (DAPI), green (eGFP), and red (non-specific) channels. Typical data treatment subtracts integrated intensities of the red channel from the specific signal in the green channel. In dose response curves for SAR studies, each compound is tested in a 5-step, 2-fold titration observing a minimum of 4 replicates wells/titer, or 36 separate images.

Example 2

Study of Small Molecule Inducers of Stem Cell Differentiation

For differentiation in the serum free Cripto$^{-/-}$ ES cell assay, cells were transferred to serum free conditions and were treated at day 2 of EB formation with Wnt3a, 15 ng/ml TGFβ2, 10 ng/ml BMP4 or 15 ng/ml Activin A in the presence of the disclosed compounds. For detection of the direct target of TGFb/Activin A (i.e., Lefty1), samples were taken 24 hr after Activin A/BMP4/TGFβ2 induction, (FIG. 1). Dihydropyridine molecules of Formula I were added at day 2 and selectively inhibited TGFβ2-induced Lefty1.

Figure 2:
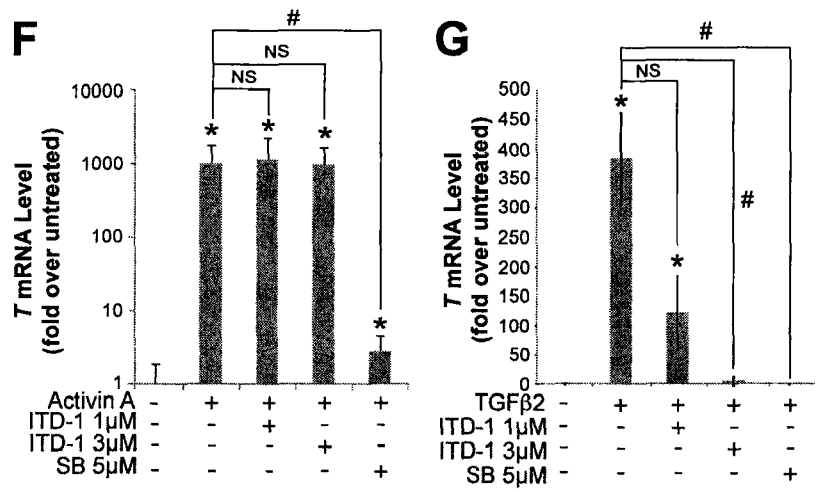
FIG. 2 graphically depicts ITD specifically blocking TGFb, but not Activin A induced mesoderm.

For differentiation in the serum free Cripto$^{-/-}$ ES cell assay, cells were transferred to serum free conditions and were treated at day 2 of EB formation with Wnt3a, 15 ng/ml TGFβ2, 10 ng/ml BMP4 or 15 ng/ml Activin A in the presence of the indicated compounds. For target genes for mesoderm induction, samples were taken after 48 h. (FIG. 2). DHP was added at day 2 and selectively inhibits TGFβ2 induced mesoderm.

Figure 3:
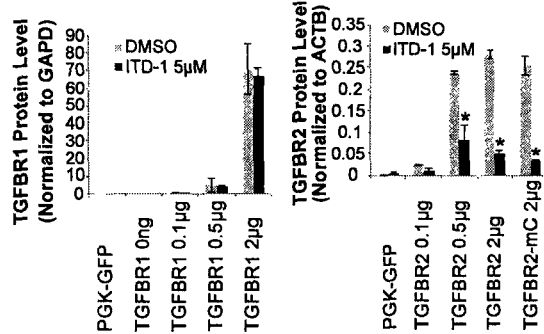
FIG. 3 is a bar graph that shows ITD specifically degrades TGFb type II receptors.

An extracellularly HA-tagged TGFBR2-mCherry fusion protein assay was developed that allowed the cell surface (extracellular HA-tag immunostaining) and total TGFBR2 abundance (mCherry fluorescence) to be measured independently in the same experiment. By flow cytometry, both HA-tag and mCherry levels declined in response to ITD-1 (FIG. 3). The effect of 7 (ITD-1) was selective for TGFBR2, since 7 (ITD-1) did not affect other transmembrane kinase receptors, including no effect on the level of the VEGF receptor-2 overexpressed in a pig endothelial cell line or on the endogenous Pdgf receptor alpha level in NIH3T3 cells. Additional support for induced degradation as the mechanism of 7 (ITD-1) action was the structure activity relationship (SAR) between TGFBR2 degradation and TGFβ2 inhibition, which was robust across 7 (ITD-1) analogs, such that TGFBR2 degradation correlated with the incidence of inhibition of TGFβ2 SBE4-Luc activity ($R^2 > 0.8$). Taken together, the 7 (ITD-1) class of molecules comprise selective TGFβ inhibitors that function by diverting TGFBR2 to the proteasome.

In another instance DHP drives cardiac differentiation of embryonic stem cells via inhibition of TGFb.

Example 3

General Synthetic Procedures for Obtaining Enantiomerically Pure Isomers of Formula I Synthesis and separation of diastereomeric esters was used to prepare optically pure material of selected dihydropyridines (DHPs) (i.e., the (+)- and (−)-enantiomers). The method used the chiral esterifying group D-threonine, that furnished 1,4-dihydropyridine diastereomers that were separated by conventional silica gel chromatography. The esters were subsequently cleaved by a β-elimination using the base DBU. As shown in Scheme 1, we adapted this method for the chiral ester part of the molecule, such as using L-threonine and a (3-NO$_2$ substituted)benzamide, as well as I$_2$-catalyzed reaction for the Hantzsch 1,4-dihydropyridine synthesis. Instead of diketene we employed 2,2,6-trimethyl-4H-1,3-dioxin-4-one for the synthesis of the chiral ester building block. For the diastereomeric mixtures we obtained good yields (50-70% range).

Scheme 1: Synthesis of (+)- and (−)-dihydropyridine enantiomers.

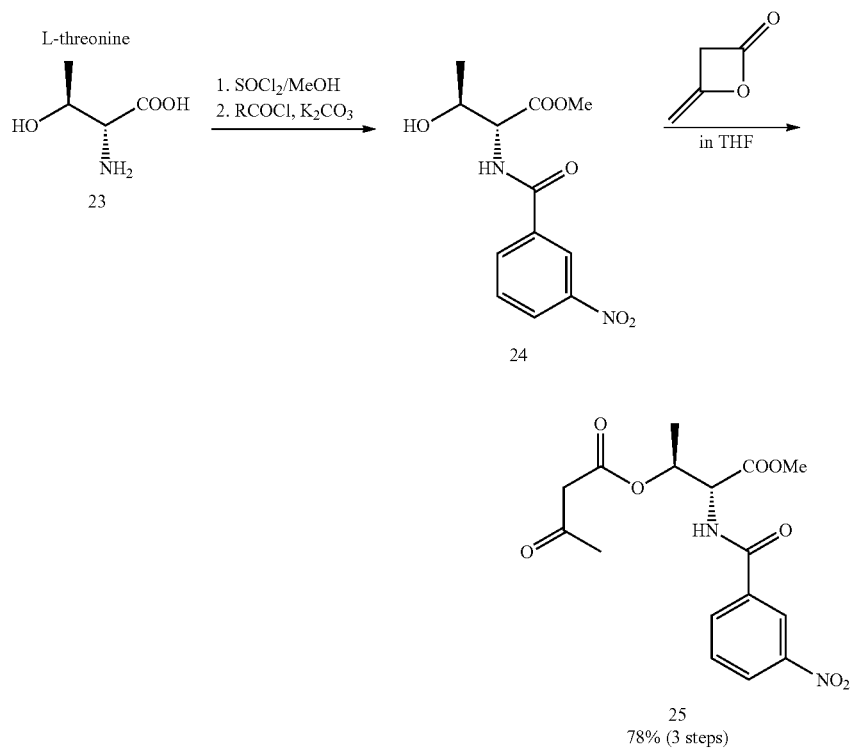

-continued
Scheme 1: Synthesis of (+)- and (−)-dihydropyridine enantiomers.
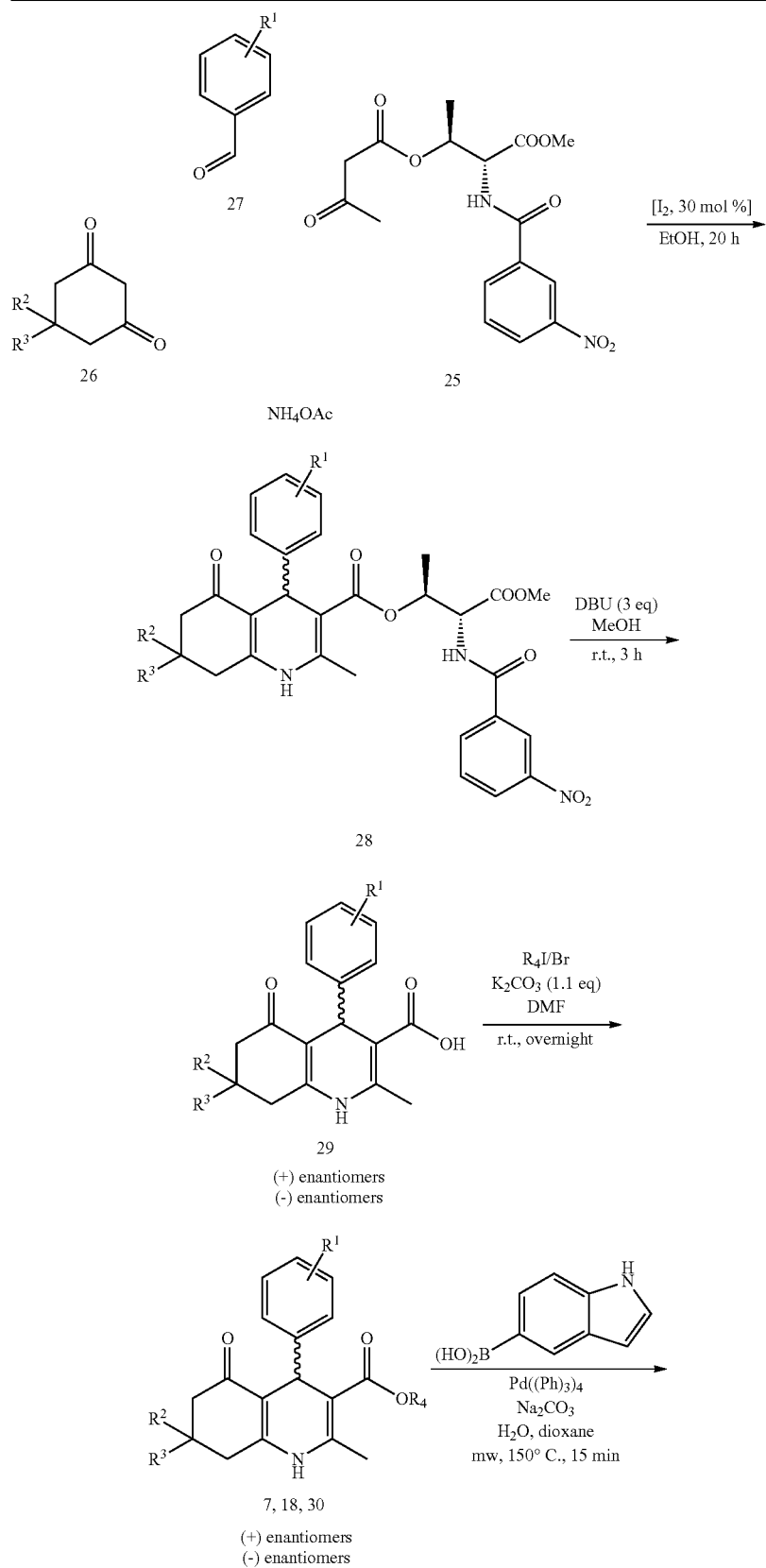

Scheme 1: Synthesis of (+)- and (−)-dihydropyridine enantiomers.

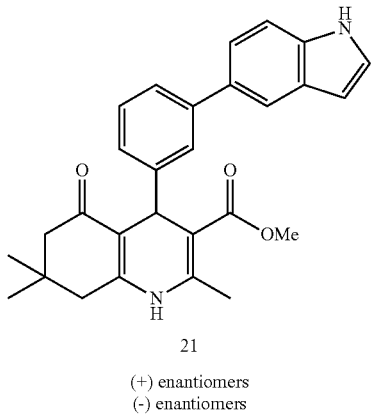 [SMILES: COC(=O)C1=C(C)NC2=C(C(=O)CC(C)(C)C2)C1c1cccc(-c2ccc3[nH]ccc3c2)c1]

21

(+) enantiomers
(−) enantiomers

| entry | $R^1$ | $R^2$ | $R^3$ | $R^4$ |
|---|---|---|---|---|
| 7 | p-Ph | Me | Me | Et |
| 18 | p-Ph | H | n-Pr | Me |
| 30 | Br | Me | Me | Me |

For esterification, an alkylation protocol was superior to other methods such as treatment of the acid in alcohol with different catalysts. The 3-(5-indole)-substituted DHP enantiomers were prepared by synthesizing and separating diastereomers on the 3-bromo intermediate basis, using the Suzuki coupling for the very last step.

Example 4

Characterization of Enantiomers of Some Compounds of Formula I

The potency and name of some of the enantiomeric pairs listed below is provided in Table 1.

Ethyl 4-(Biphenyl-4-yl)-2,7,7-trimethyl-5-oxo-1,4,5, 6,7,8-hexahydroquinoline-3-carboxylate Enantiomers (7)

137 mg (0.353 mmol) of the respective carboxylic acid enantiomer 29, 56.8 mg of $K_2CO_3$ and 45 mg of ethyl bromide (0.41 mmol) were stirred in 10 mL of dry DMF overnight at room temperature, 50 mL of water was added and the mixture extracted with EtOAc (3×). The organic layer was washed with water (1×20 mL) and brine (1×20 mL), dried ($Na_2SO_4$) and concentrated in a vacuum. The crude mixture was further purified by flash chromatography ($SiO_2$, hexanes/EtOAc: 0-60%).

7(−) Enantiomer:
Yield: 140 mg of a pale-yellow solid (95%, starting from 8a). TLC: $R_f$=0.33 (hexanes/EtOAc, 1:1); $a_D^{23}$=−70.3; % ee=≥96% ($^1$H NMR); $^1$H NMR (500 MHz, $CDCl_3$): 0.96 (s, 3H), 1.09 (s, 3H), 1.23 (t, J=7.2 Hz, 3H), 2.15-2.39 (m, 4H), 2.38 (s, 3H), 4.08 (q, J=7.2 Hz, 2H), 5.10 (s, 1H), 6.49 (bs, NH), 7.25-7.54 (m, 9H). LRMS calcd for $C_{27}H_{29}NO_3$, 416.22 (M+H). found 416.68 (M+H). HPLC purity 99.0%, $t_R$=8.19 min.

7(+) Enantiomer:
Yield: 137 mg of a pale-yellow solid (93%, starting from 8b). TLC: $R_f$=0.33 (hexanes/EtOAc, 1:1); $a_D^{23}$=+68.05; % ee=≥96% ($^1$H NMR); $^1$H NMR (500 MHz, $CDCl_3$): 0.97 (s, 3H), 1.10 (s, 3H), 1.23 (t, J=7.2 Hz, 3H), 2.16-2.40 (m, 4H), 2.41 (s, 3H), 4.08 (q, J=7.2 Hz, 2H), 5.10 (s, 1H), 5.73 (bs, NH), 7.25-7.55 (m, 9H). LRMS calcd for $C_{27}H_{29}NO_3$, 416.22 (M+H). found 416.62 (M+H). HPLC purity 100%, $t_R$=8.28 min.

Methyl 4-(Biphenyl-4-yl)-2-methyl-5-oxo-7-n-propyl-1,4,5,6,7,8-hexahydroquinoline-3-carboxylate Enantiomers (18)

18(+) Enantiomer:
The title compound was obtained according to the general procedure given for scheme 1, starting from the respective carboxylic acid 29 with 76% yield. $^1$H NMR (500 MHz, $CDCl_3$): 0.85-0.89 (m, 3H), 1.29-1.33 (m, 4H), 2.01-2.08 (m, 2H), 2.17-2.31 (m, 2H), 2.37-2.49 (m, 1H), 2.39+2.40 (2×s, 3H), 3.62 (s, 3H), 5.10+5.15 (2×s, 1H), 6.27+6.34 (2×s, 1H), 7.28 (t, J=8.4 Hz, 1H), 7.33-7.44 (m, 6H), 7.52 (br d, J=7.9 Hz, 2H). $^{13}$C NMR (500 MHz, $CDCl_3$): 19.62, 19.69, 19.83, 19.98, 33.13, 33.92, 34.14, 34.29, 36.11, 36.41, 37.68, 38.09, 43.72, 43.85, 51.27, 105.63, 105.81, 113.34, 126.98, 127.08, 127.20, 128.37, 128.48, 128.82, 139.09, 141.45, 144.07, 144.17, 146.22, 146.31, 149.47, 149.84, 162.73, 168.13, 196.03, 196.20. LRMS calcd for $C_{27}H_{29}NO_3$, 416.22 (M+H). found 416.35 (M+H). HPLC purity 100%, $t_R$=7.70 min, $a_D^{29}$=+82.31.

18(−) Enantiomer:
The title compound was obtained according to the general procedure given for scheme 1, starting from the respective carboxylic acid 29 with 83% yield. $^1$H NMR (500 MHz, $CDCl_3$): 0.86-0.89 (m, 3H), 1.28-1.33 (m, 4H), 2.01-2.08 (m, 2H), 2.17-2.30 (m, 2H), 2.37-2.47 (m, 1H), 2.39+2.40 (2×s, 3H), 3.63 (s, 3H), 5.10+5.15 (2×s, 1H), 6.43+6.49 (2×s, 1H), 7.28 (t, J=7.4 Hz, 1H), 7.33-7.44 (m, 6H), 7.51 (br d, J=7.9 Hz, 2H). $^{13}$C NMR (500 MHz, $CDCl_3$): 19.57, 19.65, 19.83, 19.97, 33.12, 34.10, 36.08, 36.42, 36.72, 37.66, 38.09, 43.73, 43.85, 51.29, 105.61, 105.77, 113.29, 126.98, 127.07, 127.19, 128.36, 128.47, 128.83, 139.09, 141.41, 144.13, 144.24, 146.24, 146.33, 149.61, 150.00, 162.75, 168.14, 196.07, 196.26. LRMS calcd for $C_{27}H_{29}NO_3$, 416.22 (M+H). found 416.35 (M+H). HPLC purity 99.7%, $t_R$=7.67 min, $a_D^{29}$=−122.46

Methyl 4-(3-(1H-indol-5-yl)phenyl)-2,7,7-trimethyl-5-oxo-1,4,5,6,7,8-hexahydroquinoline-3-carboxylate Enantiomers (21)

To a 2 mL microwave vial, 52 mg (0.129 mmol) of the respective bromo intermediate 30, 25 mg of 1H-indol-5-yl-boronic acid (0.155 mmol), 16 mg of Pd((Ph)$_3$)$_4$ catalyst, and 0.15 mL of a 2M sodium carbonate in water dioxane/water (2/1.5 mL) was heated in a microwave for 15 minutes at 150° C. Solvents were evaporated, the crude mixture dissolved in EtOAc and washed with water, dried over sodium sulfate and concentrated under reduced pressure. The crude products were purified twice by flash chromatography. For the first separation CH$_2$Cl$_2$/MeOH (0-5%) was used as the eluent and for the second hexane/EtOAc (0-60%).

21(−) Enantiomer:
Yield: 30 mg (53%) of a light-yellow solid. TLC: $R_f$=0.26 (hexane/EtOAc, 4:6); $a_D^{29}$=−49.35; LRMS calcd for $C_{28}H_{28}N_2O_3$, 441.21 (M+H). found 441.75 (M+H). HPLC purity 99.1%, $t_R$=7.55 min 21(+) Enantiomer:
Yield: 28 mg (49%) of a light-yellow solid. TLC: $R_f$=0.26 (hexane/EtOAc, 4:6); $a_D^{29}$=+48.5; LRMS calcd for $C_{28}H_{28}N_2O_3$, 441.21 (M+H). found 441.68 (M+H). HPLC purity 99.9%, $t_R$=7.62 min.

Although the disclosure has been described with reference to the above examples, it will be understood that modifications and variations are encompassed within the spirit and scope of the disclosure. Accordingly, the disclosure is limited only by the following claims.

Example 5

General Synthetic Procedures for Obtaining Compounds of Formula I

Compounds were prepared following the well established Hantsch reaction. In a typical procedure, 1 equivalent of aldehyde R4CHO, 1 eq. of substituted dimedone, 1 eq. β-ketoester and 1 eq. ammonium hydroxide was stirred in a minimum amount of ethanol and 0.3 eq. of iodine. The crude material was purified by liquid chromatography. When the desired aldehyde was not available, a Suzuki reaction was used in the same fashion as in Scheme 1 to prepare the desired aldehyde.

Figure 4:
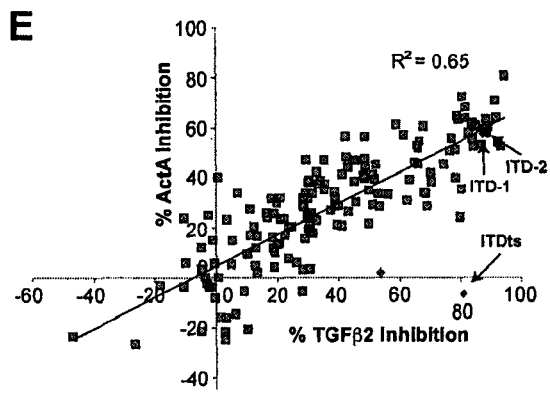
FIG. 4 is a scatter plot depicting increased TGFb selectivity of some DHPs assessed by Smad4 binding response element
Figure 5:
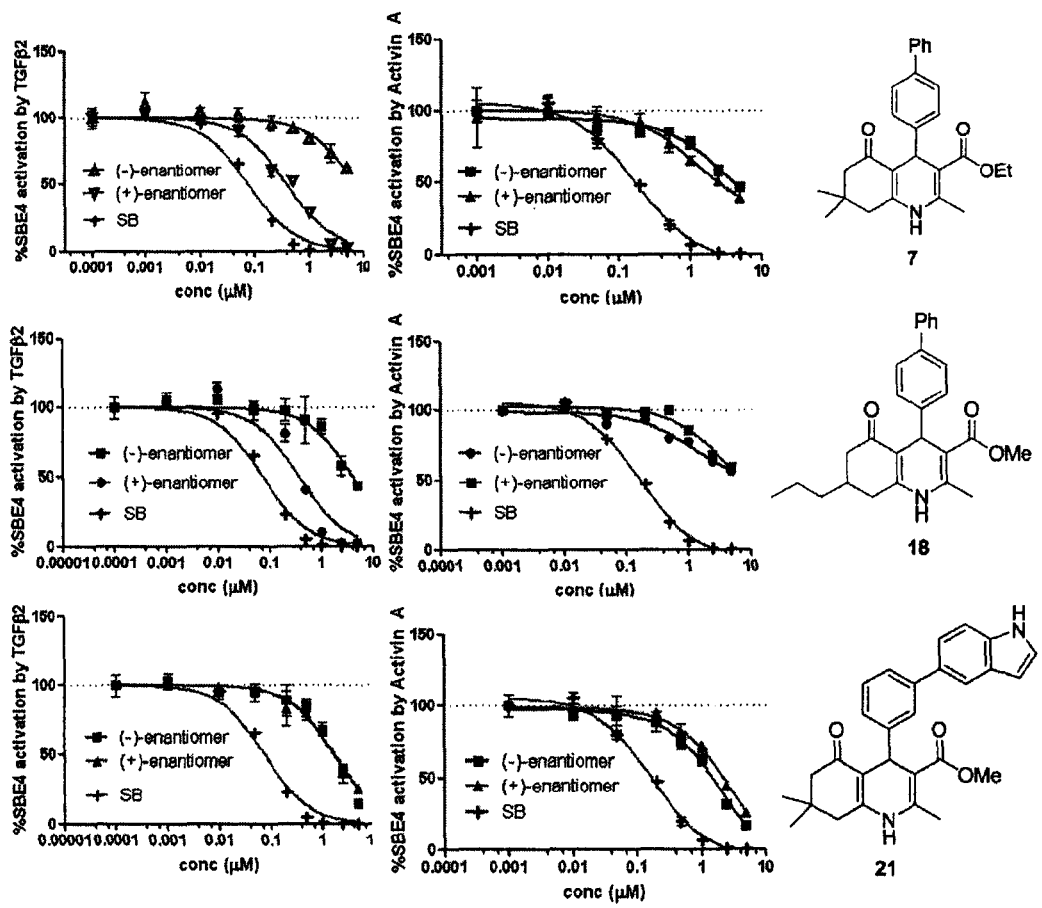
FIG. 5 is a graphic representation that shows evaluation of DHPs in Smad4 response element (SBE4).

Potency of Compounds of General Formula I, in Particular Enantiomerically Pure Isomers in TGFβ/Activin A Assays From >200 synthesized 1,4-DHPs that were screened in a transient Smad/SBE4-reporter system in 293T cells we selected about 60 DHPs for a detailed investigation of SAR for inhibition of TGFβ2 signaling (FIG. 4). For key compounds we generated additional SAR data from mESC cardiac and mesoderm inhibition assays as well as a transient TGFβRII down regulation assay in 293T cells.

Inhibition of TGFβ and Activin A Signaling.

We used a Smad-4-binding element (SBE4) reporter assay in HEK293T cells (96-well format) to evaluate compounds in a dose-dependent manner for inhibition of TGFβ-2 and activin A signaling. Briefly, a SBE-4-firefly luciferase plasmid was cotransfected together with a Renilla luciferase plasmid into HEK293T (in batch). Thereafter, cells were counted and plated on 96-well plates to minimize well-to-well differences in cell numbers and transfection efficiencies. Then cells were treated with TGFβ2 or activin A (10 ng/mL) and different doses of test compounds in comparison to DMSO controls and non-stimulated cells.

The stereochemical structure-activity relationships for TGFβ signaling inhibition was examined because 1,4-DHPs carry a center of chirality at the 4-position. Chirality at the 4-position is well-recognized as crucial for the pharmacological properties of 1,4-DHPs (e.g., the (−)-(S)-enantiomer of the calcium channel modulator BAY K8644 is approximately 10-fold more potent as a calcium channel activator compared to the (+)-(R)-antipode that acts as an antagonist). The potency of three DHPs with chirality defined a position 4 that covered a range of TGFβ inhibition potency and cardiogenic activity was investigated. These studies are representative for all of the disclosed DHPs as they all could be synthesized in enantiomeric form. Optically pure (+)- and (−)-enantiomers of 7, 18 and 21 were synthesized. The enantiomers showed a highly stereoselective interaction of the active (−)-enantiomers with their in so far unidentified cellular target/binding partner. In contrast, the (+)-enantiomers were 10- to 15-fold less potent than their (−)-antipodes (Table 1). Activin A signaling, however, was not as potently inhibited as TGFβ and did not distinguish between (+)- and (−)-enantiomers suggesting a different, presumably non-stereoselective mode of action. One surprising finding was that enantiomers of 21 did not show any of the biological stereoselectivity that was observed for enantiomers of 7 and 18. The enantiomers of 21 did not afford stereoselectivity for TGFβ or Activin A inhibition alone nor was selectivity of TGFβ over Activin A inhibition obvious.

TABLE 1

Inhibition of TGFbeta by dihydropyridines and enantiomers.

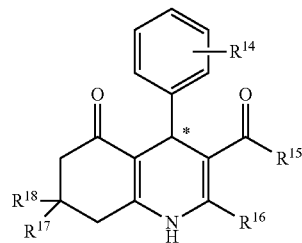

| TGFb inh. (%) | | | | | | | | |
|---|---|---|---|---|---|---|---|---|
| 2.5 μm | SD | Compound ID | $R^{14}$ | $R^{15}$ | $R^{17}$ | $R^{18}$ | $R^{16}$ | Chirality$^a$ |
| 83 | 8 | 7 | Ph | OEt | Me | Me | Me | rac |
| 30 | 3 | 7(−) | Ph | OEt | Me | Me | Me | (−) |

TABLE 1-continued

Inhibition of TGFbeta by dihydropyridines and enantiomers.

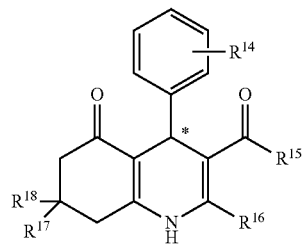

TGFb inh. (%)

| 2.5 μm | SD | Compound ID | R14 | R15 | R17 | R18 | R16 | Chirality[a] |
|---|---|---|---|---|---|---|---|---|
| 95 | 4 | 7(+) | Ph | OEt | Me | Me | Me | (+) |
| 96 | 2 | 18 | Ph | OMe | Pr | H | Me | rac |
| 97 | 1 | 18(+) | Ph | OMe | Pr | H | Me | (+) |
| 49 | 9 | 18(−) | Ph | OMe | Pr | H | Me | (−) |
| 45 | 21 | 21 | 3-(5-indoyl) | OMe | Me | Me | Me | rac |
| 54 | 9 | 21(−) | 3-(5-indoyl) | OMe | Me | Me | Me | (−) |
| 60 | 5 | 21(+) | 3-(5-indoyl) | OMe | Me | Me | Me | (+) |
| 48 | 6 | 31 | Ph | OMe | Me | H | Me | rac |
| 61 | 1 | 32 | Ph | OMe | Ph | H | Me | rac |
| 92 | 1 | 33 | Ph | OMe | Et | H | Me | rac |
| 83 | 8 | 34 | Ph | OMe | iPr | H | Me | rac |
| 94 | 2 | 35 | Ph | OMe | iBu | H | Me | rac |
| 40 | 6 | 36 | Ph | OMe | 4-N(Me)2Ph | H | Me | rac |
| 88 | 2 | 37 | 4-MePh | OMe | Me | Me | Me | rac |
| 78 | 1 | 38 | 4-(4-CO2Me)Ph | OMe | Me | Me | Me | rac |
| 59 | 1 | 39 | 4-Ph—3F—Ph | OMe | Me | Me | Me | rac |
| 18 | 4 | 40 | 4-pyrazole | OMe | Me | Me | Me | rac |
| 88 | 1 | 41 | Ph | OEt | Me | Me | n-Pr | rac |
| 52 | 1 | 2 | Ph | OMe | Me | Me | Me | rac |
| 73 | 1 | 43 | 4-(3-Cl—Ph) | OMe | Me | Me | Me | rac |
| 87 | 2 | 44 | 2-Me Ph | OMe | Me | Me | Me | rac |
| 58 | 1 | 45 | 2-F Ph | OMe | Me | Me | Me | rac |
| 91 | 6 | 46 | 4-(4-CF3—Ph) | OMe | Me | Me | Me | rac |
| 41 | 6 | 47 | 4-(5-indole) | OMe | Me | Me | Me | rac |
| 5 | 6 | 48 | 3-(4-OMePh) | OMe | Me | Me | Me | rac |
| 27 | 1 | 16 | 3-(3-ClPh) | OMe | Me | Me | Me | rae |
| 94 | 1 | 50 | 4-Cy | OMe | Me | Me | Me | rac |
| 10 | 11 | 51 | 3-(3-Py) | OMe | Me | Me | Me | rac |
| 18 | 13 | 52 | 3-Ph | OMe | Me | Me | Me | rac |
| 21 | 4 | 53 | 4-(4-Cl-3-Py) | OEt | Me | Me | Et | rac |
| 41 | 2 | 10 | 4-(2-Py) | OEt | Me | Me | Et | rac |
| 79 | 3 | 55 | 4-tBu | OMe | Me | Me | Me | rac |
| 4 |  | 11 | 4-F | OMe | Me | Me | Me | rac |
| 85 | 4 | 57 | Ph | OCH2CF3 | Me | Me | Me | rac |
| 87 | 1 | 58 | Ph | OiBu | Me | Me | Me | rac |
| 40 | 1 | 59 | Ph | NHPMB | Me | Me | Me | rac |
| 6 | 4 | 60 | H | OMe | Me | Me | Me | rac |
| 40 | 8 | 63 | Ph | O(CH2)2CH(Me)2 | Me | Me | Et | rac |
| 21 | 11 | 64 | Ph | OH | Me | Me | Me | rac |
| 96 | 0 | 17 | 4-(2-Cl—Ph) | OMe | Me | Me | Me | rac |
| 51 | 3 | 66 | 4-(5-indoyl) | OMe | Me | Me | Me | rac |
| 71 | 4 | 67 | Ph | OiPent | Me | Me | Me | rac |
| 72 | 8 | 5 | Ph | OPMB | Me | Me | Me | rac |
| 21 | 30 | 69 (N-Methyl) | Ph | OEt | Me | Me | Me | rac |
| 98 | 0 | 70 | 4-tBu | OEt | Pr | H | Me | rac |
| 94 | 1 | 71 | 4-tBu | OiBu | Pr | H | Me | rac |

[a]rac, racemic

What is claimed is:

1. A compound selected from the group consisting of: compounds having structural Formula (I):

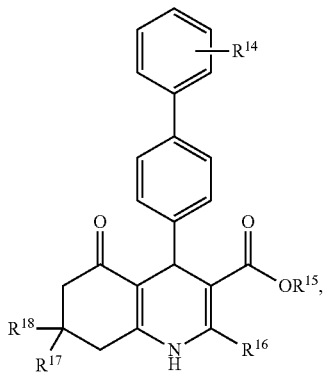

chirally pure stereoisomers, and pharmaceutically acceptable salts and solvents thereof, wherein:
- $R^{14}$ is selected from the group consisting of hydrogen, halogen, perhaloalkyl, alkyl, nitro, hydroxyl, alkoxyl, carboxyl and $C_1$-$C_6$alkyl,
- $R^{15}$ is hydrogen, $C_2$-$C_6$ alkyl, methyl prolinol, 4-ethyl piperidine, N-t-butyl carbamyl 4-ethyl piperidine, perhaloalkyl, trifluoroethyl, trifluoromethyl, benzyl, substituted benzyl, cycloalkyl or substituted cycloalkyl
- $R^{16}$ is hydrogen, $C_1$-$C_6$ alkyl, furyl or substituted furyl; and one of $R^{17}$ and $R^{18}$ is hydrogen and the other is $C_1$-$C_6$ alkyl;

and compounds having structural Formula (II):

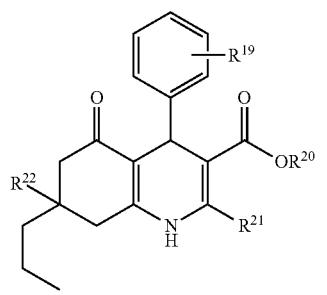

and chirally pure stereoisomers, and pharmaceutically acceptable salts and solvates thereof, wherein:
- $R^{19}$ is selected from the group consisting of hydrogen, phenyl, 3-(5-indoyl), 4-pyrazole, halogen, perhaloalkyl, alkyl, nitro, hydroxyl, alkoxyl, carboxyl and $C_1$-$C_6$alkyl, wherein phenyl, 3-(5-indoyl), and 4-pyrazole are each independently substituted with 1-3 $R^{23}$,
- $R^{20}$ is hydrogen, $C_2$-$C_6$ alkyl, methyl prolinol, 4-ethyl piperidine, N-t-butyl carbamyl 4-ethyl piperidine, perhaloalkyl, trifluoroethyl, trifluoromethyl, benzyl, substituted benzyl, cycloalkyl or substituted cycloalkyl, and
- $R^{21}$ is hydrogen, $C_1$-$C_6$ alkyl, furyl or substituted furyl;
- $R^{22}$ is hydrogen; and
- $R^{23}$ is selected from the group consisting of hydrogen, halogen, perhaloalkyl, alkyl, nitro., hydroxyl, alkoxyl, carboxyl and $C_1$-$C_6$alkyl.

2. A compound: selected from the group consisting of

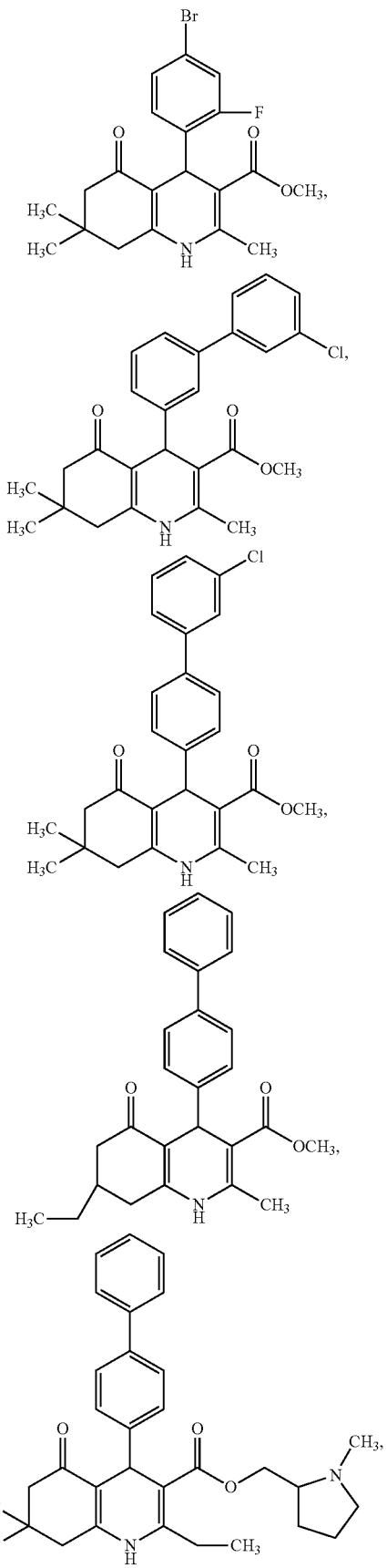

-continued

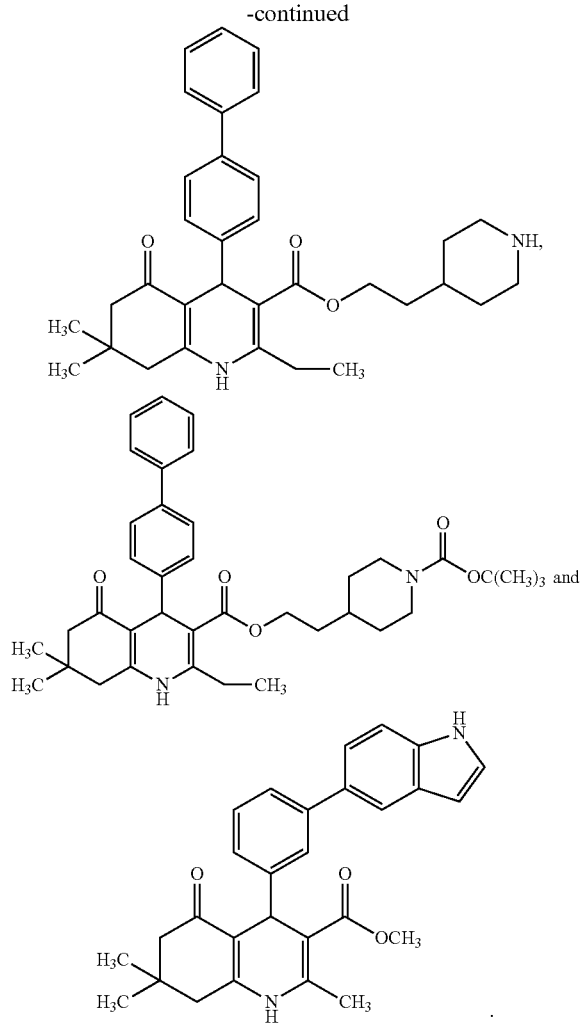

3. The compound of claim 1, wherein the pharmaceutically acceptable salt is the salt of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), or undecylenic acid.

4. The compound of claim 1, wherein the compound has structural Formula (I).

5. The compound of claim 4, wherein $R^{14}$ is hydrogen.

6. The compound of claim 4, wherein $R^{15}$ is ethyl.

7. The compound of claim 4, wherein $R^{16}$ is methyl.

8. The compound of claim 1, wherein the compound has structural Formula (II).

9. The compound of claim 8, wherein $R^{19}$ is phenyl.

10. The compound of claim 9, wherein $R^{23}$ is perhaloalkyl.

11. The compound of claim 1, wherein $R^{19}$ is hydrogen.

12. The compound of claim 11, wherein $R^{23}$ is alkyl.

* * * * *